United States Patent
Chen et al.

(10) Patent No.: US 12,259,345 B1
(45) Date of Patent: Mar. 25, 2025

(54) METHOD FOR DETERMINING REASONABLE SOAKING TIME OF SHALE OIL/GAS WELL

(71) Applicant: SOUTHWEST PETROLEUM UNIVERSITY, Sichuan (CN)

(72) Inventors: Mingjun Chen, Chengdu (CN); Zhehan Lai, Chengdu (CN); Yili Kang, Chengdu (CN); Wei Jiang, Chengdu (CN); Shunliang Zou, Wuhan (CN); Dengyu Luo, Tianjin (CN); Wangkun Cao, Xi'an (CN); Jiajia Bai, Changzhou (CN); Lijun You, Chengdu (CN); Maoling Yan, Chengdu (CN); Xingyu Tang, Chengdu (CN)

(73) Assignee: SOUTHWEST PETROLEUM UNIVERSITY, Chengdu (CN)

(*) Notice: Subject to any disclaimer, the term of this patent is extended or adjusted under 35 U.S.C. 154(b) by 0 days.

(21) Appl. No.: 18/908,785

(22) Filed: Oct. 7, 2024

Related U.S. Application Data (63) Continuation-in-part of application No. PCT/CN2024/116511, filed on Sep. 3, 2024.

(30) Foreign Application Priority Data

Nov. 15, 2023 (CN) .......................... 202311520005.2

(51) Int. Cl.
*G01N 24/08* (2006.01)
*G01N 1/34* (2006.01)
(Continued)

(52) U.S. Cl.
CPC ............. *G01N 24/081* (2013.01); *G01N 1/34* (2013.01); *G01N 1/44* (2013.01); *G01N 27/041* (2013.01); *G01N 33/24* (2013.01)

(58) Field of Classification Search
None
See application file for complete search history.

(56) References Cited

U.S. PATENT DOCUMENTS

| | | | |
|---|---|---|---|
| 5,301,751 A * | 4/1994 | Githens | .................. E21B 33/14 166/291 |
| 2019/0330980 A1* | 10/2019 | Zhu | ....................... E21B 49/003 |
| 2020/0355598 A1 | 11/2020 | Guo et al. | |

FOREIGN PATENT DOCUMENTS

| | | |
|---|---|---|
| CN | 109973037 A | 7/2019 |
| CN | 110470575 A | 11/2019 |

(Continued)

OTHER PUBLICATIONS

Lin, Hun, et al. "Dynamic displacement of adsorbed methane by fracturing fluid during soaking in a shale gas reservoir based on low-field nuclear magnetic resonance." Journal of Petroleum Science and Engineering 208 (2022): 109582 (Year: 2022).*

(Continued)

*Primary Examiner* — Lina Cordero
(74) *Attorney, Agent, or Firm* — PORUS IP LLC (57) ABSTRACT

Disclosed is a method for determining a reasonable soaking time of a shale oil/gas well, implementing testing and experimentation using a device for testing a reasonable soaking time of a shale oil/gas well. The method includes: selecting a core sample; measuring and obtaining a porosity of the core sample; simulating a state of a first core sample in a reservoir; injecting methane to reach a pore pressure of the reservoir; injecting a simulated fracturing fluid into a core gripper; measuring a resistivity change curve of the first core sample; measuring and obtaining a half-life period of pressure attenuation of a first pressure sensor until an inflection point appears in the resistivity change curve of the first core sample; obtaining an experimental duration during which the first core sample and a second core sample present (Continued)

the shortest half-life period of pressure attenuation; obtaining a time point at which core NMR signals of the first core sample and the second core sample have the largest change amplitude; obtaining soaking time at a core scale after sorting; and obtaining the soaking time of the shale oil/gas well.

5 Claims, 3 Drawing Sheets

(51) Int. Cl.
*G01N 1/44* (2006.01)
*G01N 27/04* (2006.01)
*G01N 33/24* (2006.01)

(56) References Cited

FOREIGN PATENT DOCUMENTS

| CN | 110532707 | A | | 12/2019 |
|---|---|---|---|---|
| CN | 111257202 | A | | 6/2020 |
| CN | 111948109 | A | | 11/2020 |
| CN | 112112622 | A | | 12/2020 |
| CN | 112112641 | A | | 12/2020 |
| CN | 113218834 | A | * | 8/2021 |
| CN | 113338900 | A | | 9/2021 |
| CN | 113356791 | A | | 9/2021 |
| CN | 115263286 | A | | 11/2022 |
| CN | 115639115 | A | | 1/2023 |
| CN | 115788402 | A | | 3/2023 |
| CN | 116656331 | A | | 8/2023 |
| CN | 117252127 | A | | 12/2023 |
| GB | 201513655 | | | 12/2016 |

OTHER PUBLICATIONS

CN111257202A translation (Year: 2020).*
CN113218834A translation (Year: 2021).*
First Office Action in Chinese Application No. 202311520005.2 mailed on Dec. 21, 2023, 12 pages.
Notification to Grant Patent Right for Invention in Chinese Application No. 202311520005.2 mailed on Jan. 2, 2024, 5 pages.
Zhu, Chaofan, Enhanced Shale Oil Recovery by CO2 Injection, China Doctoral Dissertations Full-text Database, 2020, 133 pages.
Wang, Qiang et al., Shut-in Time Optimization after Fracturing in Shale Oil Reservoirs, Petroleum Exploration and Development, 49(3): 586-596, 2022.

* cited by examiner

NMR region   Constant temperature   Electrical connection
             room region

FIG. 1

NMR region  Constant temperature  Electrical connection
            room region

METHOD FOR DETERMINING REASONABLE SOAKING TIME OF SHALE OIL/GAS WELL

CROSS-REFERENCE TO RELATED APPLICATIONS

This application is a Continuation-in-part of International Application No. PCT/CN2024/116511, filed on Sep. 3, 2024, which claims priority to Chinese Patent Application No. 202311520005.2, filed on Nov. 15, 2023, the entire contents of each of which are incorporated herein by reference.

TECHNICAL FIELD

The present disclosure relates to the technical field of oil and gas development, and in particular to a method for determining a reasonable soaking time of a shale oil/gas well.

BACKGROUND

Horizontal well and staged fracturing technology are effective means to realize efficient shale oil/gas development. A large amount of fracturing fluid needs to be used in the process of hydraulic fracturing. However, due to the fact that the shale reservoir is very dense, the reservoir and infiltration space is dominated by micro-nano pores, the reservoir porosity and permeability are low as a whole, and the shale foliation develops with a high content of clay mineral, which leads to a low backflow rate of fracturing fluid in the reservoir.

In the production practice and indoor research of the shale oil/gas well, it is found that if well soaking is performed for a certain period of time after the hydraulic fracturing reconstruction of the production well is completed, the initial production is higher than the situation without well soaking, and the phenomenon of "low backflow rate and high initial production" occurs.

Therefore, it is desirable to provide a method for determining a reasonable soaking time of a shale oil/gas well, which is logically simple, accurate, and reliable.

SUMMARY

One or more embodiments of the present disclosure provide a method for determining a reasonable soaking time of a shale gas well, implementing testing and experimentation using a device for testing a reasonable soaking time of a shale gas well. The device for testing the reasonable soaking time of the shale gas well may comprise an online nuclear magnetic resonance (NMR) tester, a core gripper disposed on the online NMR tester, a resistivity tester connected to the core gripper, a methane gas cylinder connected with an inlet of the core gripper, a simulated fracturing fluid injection pump connected with the inlet of the core gripper, a nitrogen gas cylinder connected with the inlet of the core gripper, a first pressure sensor connected with the inlet of the core gripper, a vacuum pump connected with the core gripper, a confining pressure pump connected with the core gripper, a second pressure sensor connected with the core gripper, a throttle valve connected with an outlet of the methane gas cylinder, a first valve connected with an outlet of the throttle valve, a third valve connected with an outlet of the first valve, a fifth valve connected with an outlet of the core gripper, and a computer control system electrically connected with the first pressure sensor, the second pressure sensor, and the core gripper, respectively. A core sample to be tested may be placed in the core gripper. The resistivity tester may be configured to detect the resistivity of the core sample to be tested in the core gripper. The online NMR tester and the core gripper may be disposed in a constant temperature room. The method for determining the reasonable soaking time of the shale gas well may comprise: S1, selecting a plurality of first core samples of which surfaces contain natural fractures and a plurality of second core samples of which surfaces do not contain the natural fractures, respectively; performing salt washing, oil washing, and drying on the plurality of first core samples and the plurality of second core samples; measuring lengths and diameters of the plurality of first core samples and the plurality of second core samples, and obtaining volumes of the plurality of first core samples and the plurality of second core samples, respectively; and measuring and obtaining the porosity Po of the plurality of first core samples and the plurality of second core samples, respectively; S2, presetting a temperature in the constant temperature room to a temperature of a reservoir in which the plurality of first core samples and the plurality of second core samples are located, placing each of the plurality of first core samples in the core gripper, activating the confining pressure pump, and applying a core confining pressure to each of the plurality of first core samples in the core gripper; vacuumizing the core gripper using the vacuum pump to simulate the state of each of the first core samples in the reservoir; S3, injecting methane into each of the plurality of first core samples in the core gripper using the methane gas cylinder until a pore pressure of the reservoir is reached, and maintaining the pressure for 4 days; S4, activating the simulated fracturing fluid injection pump and injecting simulated fracturing fluid into the core gripper; and closing the third valve; S5, activating the resistivity tester to measure a resistivity change curve of each of the plurality of first core samples; and continuously measuring and obtaining a half-life period of pressure attenuation of the first pressure sensor using a pressure attenuation method at the same time until an inflection point appears in the resistivity change curve of each of the plurality of first core samples; S6, replacing each of the plurality of first core samples in the core gripper with each of the plurality of second core samples, and repeating the operations S2-S5; and obtaining an experimental duration $t_{1f}$ during which each of the plurality of first core samples presents the shortest half-life period of pressure attenuation and an experimental duration $t_{1m}$ during which each of the plurality of second core samples presents the shortest half-life period of pressure attenuation, respectively; during a time period between the injection of the simulated fracturing fluid in the operation S4 and the appearance of the inflection point in the resistivity change curve in the operation S5, continuously monitoring methane nuclear magnetic signals of the plurality of first core samples and the plurality of second core samples using the online NMR tester, and obtaining a time point $t_{2f}$ at which the core nuclear magnetic signals of the plurality of first core samples have the largest change amplitude and a time point $t_{2m}$ at which the core nuclear magnetic signals of the plurality of second core samples have the largest change amplitude, respectively; S7, sorting the experimental duration $t_{1f}$ during which each of the plurality of first core samples presents the shortest half-life period of pressure attenuation, the experimental duration $t_{1m}$ during which each of the plurality of second core samples presents the shortest half-life period of pressure attenuation, the time point $t_{2f}$ at which the core nuclear magnetic signals of the plurality of first core samples have the largest change amplitude, and the time point $t_{2m}$, at which the core nuclear magnetic signals of the plurality of second core samples have the largest change amplitude, taking sorted two intermediate arrays as time endpoints, and a value within the time endpoints being soaking time $t_c$ at a core scale; and S8, obtaining soaking time $t_R$ of the shale gas well based on the soaking time $t_c$ at the core scale, which is expressed as:

$$t_R = t_c \frac{(V_2 - V_3)\Phi_m}{V_1 \Phi_0} \times \frac{V_c}{V_f}.$$

wherein $V_2$ denotes a total volume of reservoir reconstruction by hydraulic fracturing; $V_3$ denotes a total volume of sand spreading fractures formed in the reservoir after hydraulic fracturing; $V_c$ denotes a volume of the simulated fracturing fluid pumped to establish a target water saturation of the core; $V_1$ denotes a volume of each of the plurality of first core samples or each of the plurality of second core samples; $V_f$ denotes a volume of fracturing fluid pumped for onsite hydraulic fracturing construction; and om denotes a reservoir porosity after hydraulic fractures are removed from a total reconstruction region of hydraulic fracturing.

BRIEF DESCRIPTION OF THE DRAWINGS

The present disclosure will be further illustrated by way of exemplary embodiments, which will be described in detail by means of the accompanying drawings. These embodiments are not limiting, and in these embodiments, the same numbering indicates the same structure, wherein.

DETAILED DESCRIPTION

In order to more clearly illustrate the technical solutions of the embodiments of the present disclosure, the accompanying drawings required to be used in the description of the embodiments are briefly described below. Obviously, the accompanying drawings in the following description are only some examples or embodiments of the present disclosure, and it is possible for a person of ordinary skill in the art to apply the present disclosure to other similar scenarios in accordance with these drawings without creative labor. Unless obviously obtained from the context or the context illustrates otherwise, the same numeral in the drawings refers to the same structure or operation.

It should be understood that the terms "system", "device", "unit" and/or "module" used herein are a way to distinguish between different components, elements, parts, sections, or assemblies at different levels. However, the terms may be replaced by other expressions if other words accomplish the same purpose.

Figure 1:
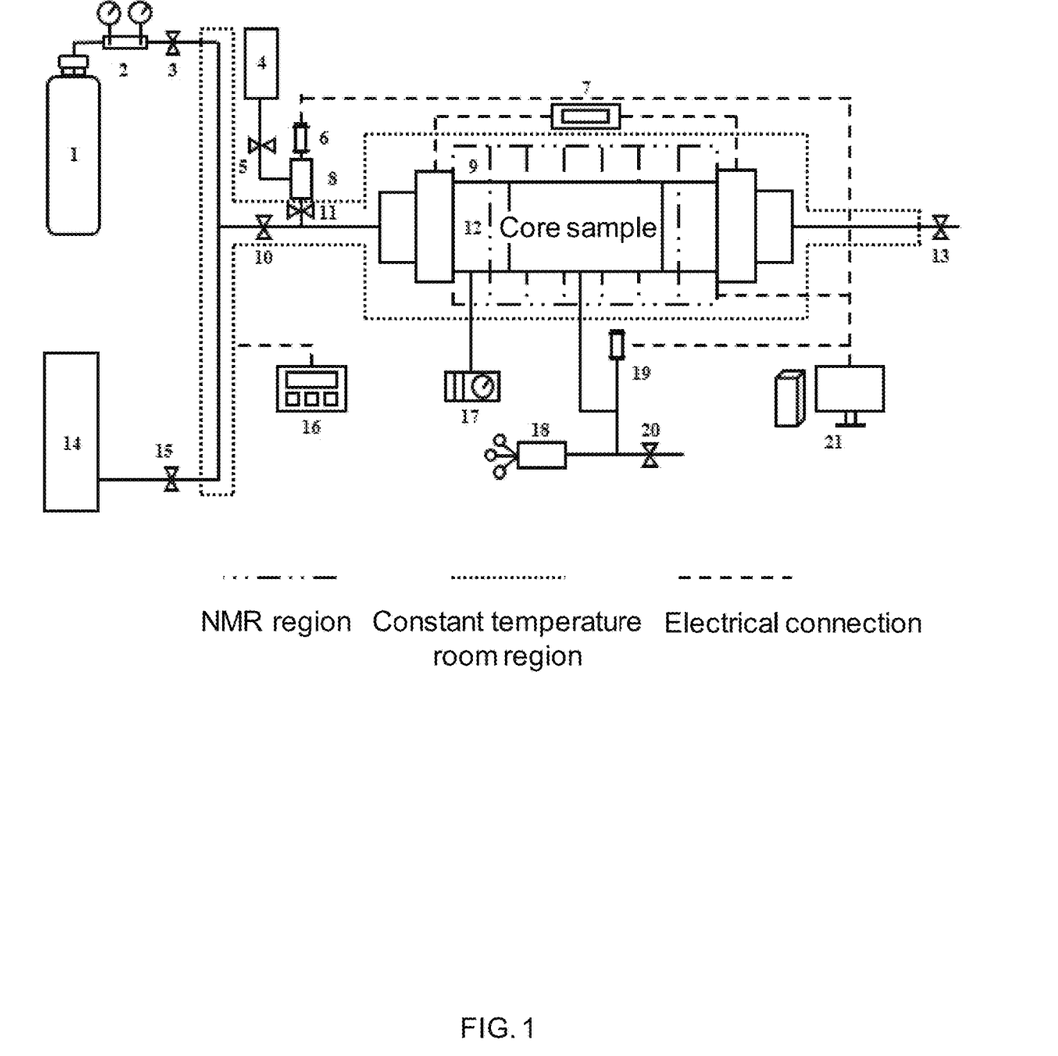
FIG. 1 is a schematic structural diagram illustrating a device for testing a reasonable soaking time of a shale gas well according to some embodiments of the present disclosure.

FIG. 1 is a schematic structural diagram illustrating a device for testing a reasonable soaking time of a shale gas well according to some embodiments of the present disclosure. It should be noted that: a region enclosed by dotted lines in FIG. 1 represents a space within a constant temperature room. In addition, dash lines represent electrical connection lines between a first pressure sensor 6, a second pressure sensor 19, and the computer control system 21. A region enclosed by double-dotted long lines represents an NMR region.

The device for testing the reasonable soaking time of the shale gas well may be configured to determine an optimal soaking time through an indoor experimental device and method under a reservoir temperature and pressure condition and considering the effect of methane adsorbed gas on the seepage of a fracturing fluid.

In some embodiments, as shown in FIG. 1, the device for testing the reasonable soaking time of the shale gas well may include an online NMR tester 9, a core gripper 12 disposed on the online NMR tester 9, a resistivity tester 7 connected to the core gripper 12, a methane gas cylinder 1 connected with an inlet of the core gripper 12, a simulated fracturing fluid injection pump 14 connected with the inlet of the core gripper 12, a nitrogen gas cylinder 4 connected with the inlet of the core gripper 12, a first pressure sensor 6 connected with the inlet of the core gripper 12, a vacuum pump 17 connected with the core gripper 12, a confining pressure pump 18 connected with the core gripper 12, a second pressure sensor 19 connected with the core gripper 12, a throttle valve 2 connected with an outlet of the methane gas cylinder 1, a first valve 3 connected with an outlet of the throttle valve 2, a third valve 10 connected with an outlet of the first valve 3, a fifth valve 13 connected with an outlet of the core gripper 12, and a computer control system 21 electrically connected with the first pressure sensor 6, the second pressure sensor 19, and the core gripper 12, respectively. A core sample to be tested may be placed in the core gripper 12. The resistivity tester 7 may be configured to detect a resistivity of the core sample to be tested in the core gripper 12. The online NMR tester 9 and the core gripper 12 may be disposed in a constant temperature room 16.

The online NMR tester 9 refers to a device for monitoring a nuclear magnetic signal, such as monitoring a methane nuclear magnetic signal, etc. In some embodiments, the online NMR tester 9 may be configured to monitor the methane nuclear magnetic signal of a first core sample and a second core sample, respectively. More descriptions regarding the first core sample and the second core sample may be found in the present disclosure below. In some embodiments, the online NMR tester 9 may be disposed in the constant temperature room 16. The constant temperature room 16 refers to a device for providing a stable temperature environment. In some embodiments, the constant temperature room 16 may be an enclosed space with an internal temperature that is constant within a preset temperature range. The preset temperature range may be determined based on manual experience. More descriptions regarding the constant temperature room 16 may be found in the present disclosure below.

The core gripper 12 refers to a device for placing a core sample. In some embodiments, the core sample to be tested may be placed in the core gripper 12. For example, the core gripper 12 may be configured to place the first core sample and the second core sample. In some embodiments, the core gripper 12 may be disposed on the online NMR tester 9. In some embodiments, the core gripper 12 may be disposed in the constant temperature room 16.

The resistivity tester 7 refers to a device for measuring the resistivity. In some embodiments, the resistivity tester 7 may be connected to the core gripper 12. In some embodiments, the resistivity tester 7 may be configured to detect the resistivity of the core sample to be tested in the core gripper 12. For example, the resistivity tester 7 may measure a resistivity change curve of the first core sample.

The methane gas cylinder 1 refers to a device for storing and transporting methane gas. For example, the methane gas cylinder 1 may be configured to inject methane into the first core sample. In some embodiments, the methane gas cylinder 1 may be connected with the inlet of the core gripper 12.

The simulated fracturing fluid injection pump 14 refers to a device for injecting a simulated fracturing fluid. For example, the simulated fracturing fluid injection pump 14 may be configured to inject the simulated fracturing fluid into the core gripper 12. In some embodiments, the simulated fracturing fluid injection pump 14 may be connected with the inlet of the core gripper 12.

The simulated fracturing fluid refers to a fluid used to simulate an actual fracturing process on a core sample. In some embodiments, the simulated fracturing fluid may include a base fluid, such as ionized water, etc. In some embodiments, the simulated fracturing fluid may include a thickener, such as guar gum, etc. In some embodiments, the simulated fracturing fluid may include a cross-linking agent, such as boric acid, etc. In some embodiments, the simulated fracturing fluid may include a gum breaker, such as ammonium persulfate, etc.

The nitrogen gas cylinder 4 refers to a device for storing and transporting high-pressure nitrogen. In some embodiments, the nitrogen gas cylinder 4 may be configured to be connected with the inlet of the core gripper 12.

The first pressure sensor 6 refers to a device for collecting pressure data. In some embodiments, the first pressure sensor 6 may be configured to collect the pressure data within the core gripper 12. In some embodiments, the first pressure sensor 6 may be configured to be connected with the core gripper 12, as shown in FIG. 1.

The vacuum pump 17 refers to a device that is used to perform vacuumizing. In some embodiments, the vacuum pump 17 may be configured to vacuumize the core gripper 12 to simulate the state of the core sample in a reservoir. The reservoir refers to a formation of a subsurface rock layer capable of storing and producing oil and gas. In some embodiments, the vacuum pump 17 may be configured to be connected with the core gripper 12, as shown in FIG. 1.

The confining pressure pump 18 refers to a device for applying a core confining pressure to the core gripper. In some embodiments, the confining pressure pump 18 may be configured to apply the core confining pressure to the core sample. The core confining pressure refers to an external pressure applied to the core sample to simulate an actual pressure environment of the reservoir on the core. In some embodiments, the confining pressure pump 18 may be configured to be connected with the core gripper 12, as shown in FIG. 1.

The second pressure sensor 19 refers to a device for collecting pressure data. In some embodiments, the second pressure sensor 19 may be configured to be connected with the core gripper 12, as shown in FIG. 1.

The throttle valve 2 refers to a valve for adjusting the flow rate and pressure of the methane gas cylinder 1. In some embodiments, the throttle valve 2 may be configured to be connected with an outlet of the methane gas cylinder 1 and an inlet of the first valve 3, as shown in FIG. 1. In some embodiments, the throttle valve 2 may be configured to adjust a methane flow rate of the methane gas cylinder 1.

The first valve 3 refers to a valve for adjusting the flow rate and pressure of the methane gas cylinder 1. In some embodiments, the first valve 3 may be configured to be connected with an outlet of the throttle valve 2. For example, the inlet of the first valve 3 may be connected with the outlet of the throttle valve 2, as shown in FIG. 1.

The third valve 10 refers to a valve for adjusting a gas, a fluid, or the like, to enter the core gripper 12. In some embodiments, the third valve 10 may be configured to be connected with an outlet of the first valve 3 and an outlet of a sixth valve 15, as shown in FIG. 1.

The fifth valve 13 refers to a valve for adjusting the outflow of a gas, a fluid, or the like, from the core gripper 12. In some embodiments, the fifth valve 13 may be configured to be connected with the outlet of the core gripper 12, as shown in FIG. 1.

The computer control system 21 refers to a device for processing and storing data associated with the device for testing the reasonable soaking time of the shale gas well. For example, the computer control system 21 may be configured to obtain temperature data collected by a temperature sensor, pressure data collected by a pressure monitoring device, an analysis result generated by an image analysis device, etc. In some embodiments, the computer control system 21 may be connected with the first pressure sensor 6, the second pressure sensor 19, and the core gripper 12, respectively.

In some embodiments, a second valve 5, a buffer container 8, and a fourth valve 11 may be connected in series between the nitrogen gas cylinder 4 and the core gripper 12, as shown in FIG. 1. The second valve 5 refers to a device for controlling nitrogen gas entering the core gripper 12. The fourth valve 11 refers to a device for controlling the nitrogen gas entering the core gripper 12. The buffer container 8 refers to a device for temporarily storing the nitrogen gas. In some embodiments, an inlet and an outlet of the buffer container 8 may be connected with an outlet of the second valve 5 and an inlet of the fourth valve 11, respectively, as shown in FIG. 1.

By configuring the second valve and the fourth valve, the speed of the nitrogen gas entering the core gripper can be adjusted; by using the buffer container, the pressure fluctuation when the nitrogen gas flows into the core gripper can be reduced, thereby ensuring that nitrogen gas is injected into the core gripper more smoothly.

In some embodiments, the sixth valve 15 may be provided between the simulated fracturing fluid injection pump 14 and the third valve 10. The sixth valve 15 refers to a device for regulating the outflow of the simulated fracturing fluid. In some embodiments, an inlet of the sixth valve 15 may be connected with the simulated fracturing fluid injection pump 14, and an outlet of the sixth valve 15 may be connected with an inlet of the third valve 10.

By configuring the sixth valve, the flow rate and speed of the simulated fracturing fluid injected into the core sample can be adjusted, making the simulated reservoir condition more realistic.

In some embodiments, a seventh valve 20 may be provided on the confining pressure pump 18. The seventh valve 20 refers to a device for adjusting the core confining pressure applied by the confining pressure pump 18. In some embodiments, an inlet of the seventh valve 20 may be connected with the confining pressure pump 18.

By configuring the seventh valve, the core confining pressure applied by the confining pressure pump can be adjusted, making the simulated core confining pressure more in line with the actual scenario.

In some embodiments, the device for testing the reasonable soaking time of the shale gas well may further include a processor. In some embodiments, the processor may be provided in the computer control system 21 or integrated in other devices of the device for testing the reasonable soaking time of the shale gas well. In some embodiments, the processor may be in communication connection with various devices of the device for testing the reasonable soaking time of the shale gas well. For example, the processor may be in communication connection with the online NMR tester 9, the resistivity tester 7, the first pressure sensor 6, and the second pressure sensor 19.

In some embodiments, the processor may be a computer, a user console, a single processor, or a group of processors, or the like. The group of processors may be centralized or distributed. In some embodiments, the processor may be implemented on a cloud platform. For example, the cloud platform may include one of a private cloud, a public cloud, a hybrid cloud, or the like, or any combination thereof.

In some embodiments, the device for testing the reasonable soaking time of the shale gas well may further include an automatic brushing device. The automatic brushing device refers to a device for cleaning the core sample. In some embodiments, the automatic brushing device may be configured to perform operations such as salt washing, oil washing, and drying on the core sample. Salt washing refers to removing residual salt from the core sample. Oil washing refers to removing oil from a surface and pores of the core sample. Drying refers to removing water from the core sample to achieve a dry state.

In some embodiments, the automatic brushing device may include a core fixing assembly, a rotation assembly, and a cleaning brush.

The core fixing assembly refers to a device for fixing the core sample. For example, the core fixing assembly may include adjustable clamps capable of being adjusted according to the size and shape of the core sample.

The rotation assembly refers to a device for driving the core sample and/or the cleaning brush to rotate. In some embodiments, the rotation assembly may include a power source, such as a pneumatic motor, an electric motor, etc. In some embodiments, the rotation assembly may include a transmission mechanism, such as a conveyor belt, a coupler, etc. Merely by way of example, the power source may drive the rotation assembly to rotate to transmit a rotational force to the core sample and/or the cleaning brush through the transmission mechanism.

The cleaning brush refers to a device for removing dirt and impurities from the surface of the core sample. In some embodiments, bristles of the cleaning brush may be made of a highly elastic and abrasion-resistant material, such as nylon, polyester fibers, and other materials. In some embodiments, the cleaning brush may be disposed on the rotation assembly to contact the core sample through a rotational motion, thereby improving the cleaning efficiency.

In some embodiments, the constant temperature room 16 may include a temperature control device, a temperature sensor, and an audible and visual alarm.

The temperature control device refers to a device for adjusting the temperature of the constant temperature room 16. In some embodiments, the temperature control device may be configured to adjust the temperature of an internal environment of the constant temperature room 16 to maintain a constant temperature within the room, thereby ensuring the accuracy in the test.

In some embodiments, the temperature control device may include a heating component, and a heat dissipation fan. The heating component refers to a device for raising the temperature of the internal environment of the constant temperature room 16, such as a resistance wire, an electric heater, etc. The heat dissipation fan refers to a device for reducing the temperature of the internal environment of the constant temperature room 1, such as a fan, etc.

The temperature sensor refers to a device for collecting temperature data. In some embodiments, the temperature sensor may be configured to collect the temperature data of the internal environment of the constant temperature room 16. For example, the temperature sensor may collect the temperature data based on a preset collection frequency to obtain the temperature data based on time series. The preset collection frequency may be preset based on manual experience.

In some embodiments, the temperature sensor may be configured to be in communication connection with the computer control system 21. In some embodiments, the temperature sensor may upload the collected temperature data to the computer control system 21.

The audible and visual alarm refers to a device that is used to give a warning. In some embodiments, the audible and visual alarm may emit an audible warning and/or a light warning. In some embodiments, the audible and visual alarm may be disposed on an external wall of the constant temperature room 16. In some embodiments, the audible and visual alarm may be configured to be in communication connection with a processor of the computer control system 21.

More descriptions regarding the audible and visual alarm may be found in the related descriptions below.

In some embodiments, the constant temperature room 16 may further include a concentration monitoring device. The concentration monitoring device refers to a device for monitoring the concentration of a gas. In some embodiments, the concentration monitoring device may be configured to collect concentration data of a methane gas in the constant temperature room 16.

In some embodiments, the concentration monitoring device may include a methane gas sensor, etc. The gas sensor refers to a sensor used to sense the methane gas in the air, such as an electrochemical sensor, a catalytic combustion sensor, an infrared sensor, etc.

In some embodiments, the concentration monitoring device may be configured to be in communication connection with the processor of the computer control system 21. In some embodiments, the concentration monitoring device may upload the collected concentration data of the methane gas to the computer control system 21.

In some embodiments, the core gripper 12 may further include a pressure monitoring device. In some embodiments, the pressure monitoring device may be disposed in the core gripper 12. The pressure monitoring device refers to a device for monitoring pressure. In some embodiments, the pressure monitoring device may be configured to monitor a gas pressure within the core gripper 12. For example, the pressure monitoring device may be configured to monitor the pressure data of the methane gas.

In some embodiments, the pressure monitoring device may be configured to be in communication connection with the processor of the computer control system 21.

In some embodiments, the device for testing the reasonable soaking time of the shale gas well may further include a photographing device and an image analysis device. In some embodiments, the photographing device may be in communication connection with the image analysis device. In some embodiments, the photographing device and the image analysis device may all be configured to be in communication connection with the processor of the computer control system 21.

The photographing device refers to a device for collecting image data. In some embodiments, the photographing device may be configured to collect an apparent image of the core sample. For example, the photographing device may capture an image and/or a video of the core sample. The apparent image of the core sample refers to a visual image of an outer surface of the core sample. In some embodiments, the collected image data may be sent to the image analysis device and/or the processor.

The image analysis device refers to a device for analyzing an image. In some embodiments, the image analysis device may be configured to generate an analysis result (e.g., fracture distribution information, etc.) based on the apparent image of the core sample. In some embodiments, the image analysis device may be configured to send the analysis result to the processor.

More descriptions regarding the photographing device, the image analysis device, and the fracture distribution information may be found in the related descriptions below.

In some embodiments of the present disclosure, with application of the device for testing the reasonable soaking time of the shale gas well, the state change of the core sample in the reservoir can be simulated more realistically, so as to make the experimental result closer to the actual situation; by collecting various data of the core sample, data support can be provided for evaluating the reasonable soaking time.

Figure 2:
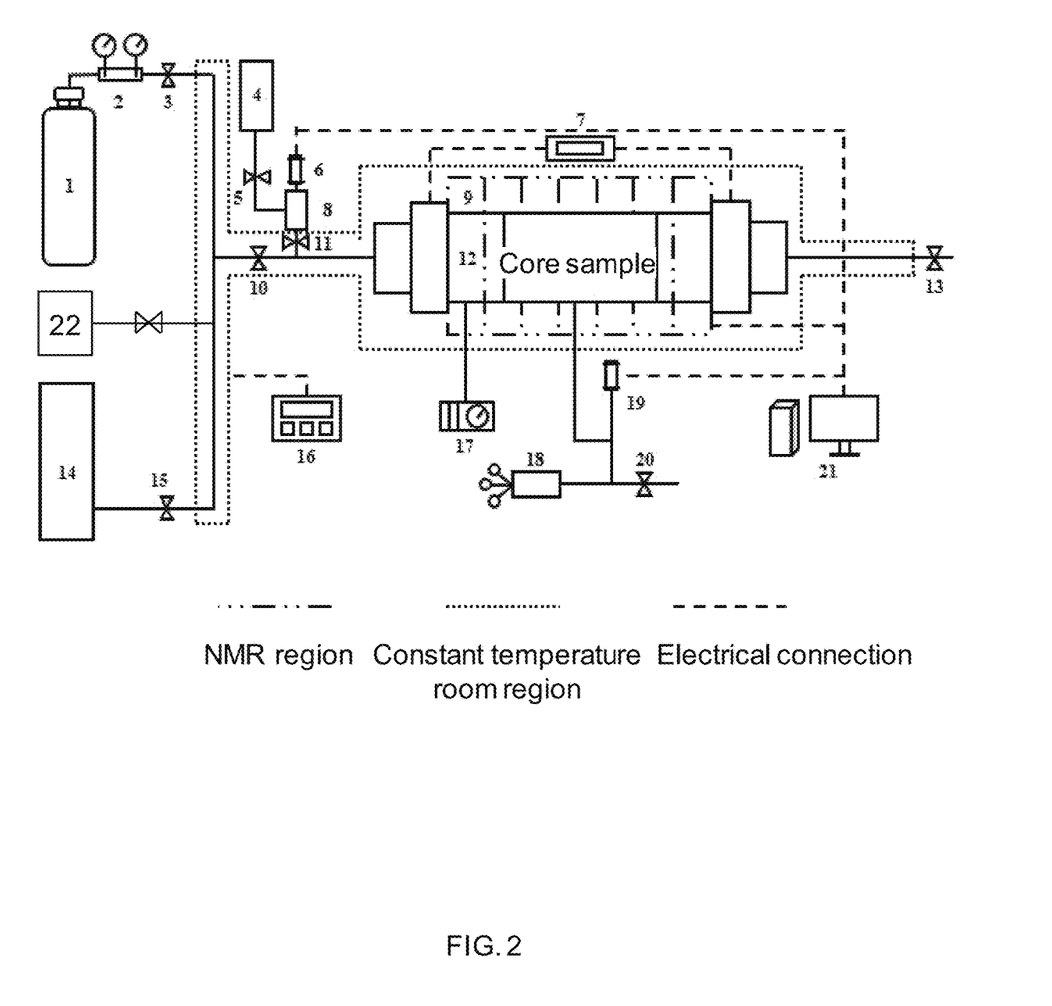
FIG. 2 is a schematic structural diagram illustrating a device for testing a reasonable soaking time of a shale oil well according to some embodiments of the present disclosure.

FIG. 2 is a schematic structural diagram illustrating a device for testing a reasonable soaking time of a shale oil well according to some embodiments of the present disclosure.

In some embodiments, as shown in FIG. 2, the device for testing the reasonable soaking time of the shale oil well may include the methane gas cylinder 1, the throttle valve 2, the first valve 3, the nitrogen gas cylinder 4, the second valve 5, the first pressure sensor 6, the resistivity tester 7, the buffer container 8, the online NMR tester 9, the third valve 10, the fourth valve 11, the core gripper 12, the fifth valve 13, the simulated fracturing fluid injection pump 14, the sixth valve 15, the constant temperature room 16, the vacuum pump 17, the confining pressure pump 18, the second pressure sensor 19, the seventh valve 20, the computer control system 21, and a simulated crude oil injection pump 22. The methane gas cylinder 1, the throttle valve 2, the first valve 3, the nitrogen gas cylinder 4, the second valve 5, the first pressure sensor 6, the resistivity tester 7, the buffer container 8, the online NMR tester 9, the third valve 10, the fourth valve 11, the core gripper 12, the fifth valve 13, the simulated fracturing fluid injection pump 14, the sixth valve 15, the constant temperature room 16, the vacuum pump 17, the confining pressure pump 18, the second pressure sensor 19, the seventh valve 20, and the computer control system 21 have the same or similar structures and functions as in FIG. 1, which are not repeated here.

The simulated crude oil injection pump 22 may be configured to inject simulated crude oil. In some embodiments, the simulated crude oil injection pump 22 may be connected with an inlet of the core gripper 12 for injecting the simulated crude oil into a core sample in the core gripper 12 until a reservoir pore pressure is reached. The simulated crude oil refers to a fluid used to simulate reservoir crude oil.

With application of the device for testing the reasonable soaking time of the shale oil well, the state change of the core sample in the reservoir can be realistically simulated for the shale oil well, which makes the experimental result closer to the actual situation. With collection of various data of the core sample, data support can be provided for evaluating the reasonable soaking time.

In some embodiments, the method for determining the reasonable soaking time of the shale gas well may be tested using the device for testing the reasonable soaking time of the shale gas well. In some embodiments, the method for determining the reasonable soaking time of the shale gas well may be performed by the computer control system 21. It should be noted that determining the reasonable soaking time of the shale oil well may be performed by a method similar to the method for determining the reasonable soaking time of the shale gas well described below, which performs the testing using the device for testing the reasonable soaking time of the shale oil well, as described below.

In S1, a plurality of first core samples of which surfaces contain natural fractures and a plurality of second core samples of which surfaces do not contain the natural fractures may be selected, respectively; salt washing, oil washing, and drying may be performed on the plurality of first core samples and the plurality of second core samples; lengths and diameters of the plurality of first core samples and the plurality of second core samples may be measured, and volumes of the plurality of first core samples and the plurality of second core samples may be obtained, respectively; and the porosity Po of the plurality of first core samples and the plurality of second core samples may be measured and obtained, respectively.

In some embodiments, the computer control system 21 may control an automatic brushing device to perform salt washing, oil washing, and drying on the plurality of first core samples and the plurality of second core samples. For example, a processor of the computer control system 21 may generate a brushing command and send the brushing command to the automatic brushing device to instruct the automatic brushing device to perform salt washing, oil washing, and drying on the plurality of first core samples and the plurality of second core samples.

In some embodiments, the computer control system 21 may control a measurement assembly to measure the lengths and the diameters of the plurality of first core samples and the plurality of second core samples. For example, the measurement assembly may send the measured lengths and diameters of the plurality of first core samples, and the lengths and the diameters of the plurality of second core samples to the processor of the computer control system 21.

In some embodiments, the processor of the computer control system 21 may correspondingly calculate the volumes of the plurality of first core samples and the plurality of second core samples based on the lengths and the diameters of the plurality of first core samples and the plurality of second core samples. For example, the processor may calculate the volumes of the plurality of first core samples and the plurality of second core samples based on the lengths and the diameters of the plurality of first core samples and the lengths and the diameters of the plurality of second core samples by means of a geometric formula (e.g., a cylinder volume formula, etc.).

In some embodiments, the computer control system 21 may control the measurement assembly to measure and obtain the porosity Po of the plurality of first core samples and the plurality of second core samples, respectively. For example, the computer control system 21 may measure the porosity of the plurality of first core samples and the plurality of second core samples, respectively, through a porosity tester.

The measurement assembly refers to a device for measuring a dimension of a core sample. In some embodiments, the measurement assembly may be configured to measure the length, the diameter, the porosity, or the like, of the core sample. For example, the measurement assembly may include a vernier caliper, a laser range finder, a porosity tester, or the like. In some embodiments, the measurement component may be in communication connection with the processor of the computer control system 21.

In S2, a temperature in the constant temperature room 16 may be preset to a temperature of a reservoir in which the plurality of first core samples and the plurality of second core samples are located, each of the plurality of first core samples may be placed in the core gripper 12, the confining pressure pump 18 may be activated, and a core confining pressure may be applied to each of the plurality of first core samples in the core gripper 12; the core gripper 12 may be vacuumized using the vacuum pump 17 to simulate the state of each of the first core samples in the reservoir.

In some embodiments, the computer control system 21 may preset the temperature in the constant temperature room 16 to the temperature of the reservoir in which the plurality of first core samples and the plurality of second core samples are located by controlling a temperature control device.

In some embodiments, the computer control system 21 may control the confining pressure pump 18 to apply the core confining pressure to the plurality of first core samples in the core gripper 12. For example, the processor of the computer control system 21 may generate a pressure applying command and send the pressure applying command to the confining pressure pump 18. The confining pressure pump 18 may, upon receiving the pressure applying command, apply the core confining pressure.

In some embodiments, the computer control system 21 may vacuumize the core gripper 12 by the vacuum pump 17 to simulate the state of the plurality of first core samples in the reservoir. For example, the processor of the computer control system 21 may generate a vacuuming command and send the vacuuming command to the vacuum pump 17. The vacuum pump 17 may, upon receiving the vacuuming command, vacuumize the core gripper 12.

In S3, methane may be injected into each of the plurality of first core samples in the core gripper 12 using the methane gas cylinder 1 until a pore pressure of the reservoir is reached, and the pressure may be maintained for 4 days.

In some embodiments, the computer control system 21 may control the methane gas cylinder 1 to inject the methane into the plurality of first core samples in the core gripper 12. For example, the processor of the computer control system 21 may cause the methane gas cylinder 1 to input the methane into the core gripper 12 by opening the throttle valve 2, as shown in FIG. 1.

It is understood that the operation S3 is directed to the shale gas well, and for the shale oil well, the computer control system 21 may control the simulated crude oil injection pump 22 to inject the simulated crude oil into the plurality of first core samples in the core gripper 12 until the pore pressure of the reservoir is reached, and the pressure may be maintained for 4 days. For the shale oil well, other operations except the operation S3 are the same as those for the shale gas well to determine the reasonable soaking time.

In S4, the simulated fracturing fluid injection pump 14 may be activated, and a simulated fracturing fluid may be injected into the core gripper 12; and the third valve 10 may be closed.

In some embodiments, the computer control system 21 may control the simulated fracturing fluid injection pump 14 to inject the simulated fracturing fluid into the core gripper 12. For example, as shown in FIG. 1, the processor of the computer control system 21 may cause the simulated fracturing fluid to flow from an outlet of the simulated fracturing fluid injection pump 14 to the core gripper 12 by opening the sixth valve 15 and the third valve 10. After the injection is completed, the processor may close the third valve 10 to stop injecting the simulated fracturing fluid into the core gripper 12.

In S5, the resistivity tester 7 may be activated to measure a resistivity change curve of each of the plurality of first core samples; and a half-life period of pressure attenuation of the first pressure sensor may be continuously measured and obtained using a pressure attenuation method at the same time until an inflection point appears in the resistivity change curve of each of the plurality of first core samples.

In some embodiments, the computer control system 21 may measure a resistivity change curve of a core sample through the resistivity tester 7. For example, the processor of the computer control system 21 may generate a resistivity test starting command and send the resistivity test starting command to the resistivity tester 7. The resistivity tester 7 may, upon receiving the resistivity test starting command, measure the resistivity change curve of the core sample (e.g., the plurality of first core samples and the plurality of second core samples).

In some embodiments, the computer control system 21 may determine the half-life period of the pressure attenuation of the first pressure sensor 6 in various ways. For example, the processor may obtain the half-life period of the pressure attenuation of the first pressure sensor 6 as measured by the pressure attenuation method until the inflection point appears in the resistivity change curve of each of the plurality of first core samples.

In S6, each of the plurality of first core samples in the core gripper may be replaced with each of the plurality of second core samples, and the operations S2-S5 may be repeated; and an experimental duration $t_{1f}$ during which each of the plurality of first core samples presents the shortest half-life period of pressure attenuation and an experimental duration $t_{1m}$ during which each of the plurality of second core samples presents the shortest half-life period of pressure attenuation may be obtained, respectively.

During a time period between the injection of the simulated fracturing fluid in the operation S4 and the appearance of the inflection point in the resistivity change curve in the operation S5, methane nuclear magnetic signals of the plurality of first core samples and the plurality of second core samples may be continuously monitored using the online NMR tester 9, and a time point $t_{2f}$ at which the core nuclear magnetic signals of the plurality of first core samples have the largest change amplitude and a time point $t_{2m}$ at which the core nuclear magnetic signals of the plurality of second core samples have the largest change amplitude may be obtained, respectively.

In S7, the experimental duration $t_{1f}$ during which each of the plurality of first core samples presents the shortest half-life period of pressure attenuation, the experimental duration $t_{1m}$ during which each of the plurality of second core samples presents the shortest half-life period of pressure attenuation, the time point $t_{2f}$ at which the core nuclear magnetic signals of the plurality of first core samples have the largest change amplitude, and the time point $t_{2m}$ at which the core nuclear magnetic signals of the plurality of second core samples have the largest change amplitude may be sorted, sorted two intermediate arrays may be taken as time endpoints, and a value within the time endpoints may be soaking time $t_c$ at a core scale.

In some embodiments, the computer control system 21 may sort an endpoint time point $t_{1f}$ corresponding to the experimental duration $t_{1f}$ during which each of the plurality of first core samples presents the shortest half-life period of pressure attenuation, an endpoint time point $t_{1m}$ corresponding to the experimental duration $t_{1m}$ during which each of the plurality of second core samples presents the shortest half-life period of pressure attenuation, the time point $t_{2f}$ at which the core nuclear magnetic signals of the plurality of first core samples have the largest change amplitude, and the time point $t_{2m}$ at which the core nuclear magnetic signals of the plurality of second core samples have the largest change amplitude may be sorted, for example, in a descending order of time points. In some embodiments, the processor may take the sorted two intermediate arrays as the time endpoints based on a sorting result, and take the value within the time endpoints as the soaking time $t_c$ at the core scale.

In S8, soaking time $t_R$ of the shale gas well may be obtained based on the soaking time $t_c$ at the core scale.

In some embodiments, the computer control system 21 may determine the soaking time $t_R$ of the shale gas well based on the soaking time $t_c$ at the core scale in various ways. For example, the processor of the computer control system 21 may determine the soaking time $t_R$ of the shale gas well based on the following equation (1):

$$t_R = t_c \frac{(V_2 - V_3)\Phi_m}{V_1 \Phi_0} \times \frac{V_c}{V_f} \quad (1)$$

wherein $V_2$ denotes a total volume of reservoir reconstruction by hydraulic fracturing; $V_3$ denotes a total volume of sand spreading fractures formed in the reservoir after hydraulic fracturing; $V_c$ denotes a volume of the simulated fracturing fluid pumped to establish a target water saturation of the core; $V_1$ denotes a volume of the core sample (e.g., each of the plurality of first core samples or each of the plurality of second core samples, etc.); $V_f$ denotes a volume of fracturing fluid pumped for onsite hydraulic fracturing construction; and $\Phi_m$ denotes a reservoir porosity after hydraulic fractures are removed from a total reconstruction region of hydraulic fracturing.

In some embodiments, the computer control system 21 may determine the volume of the injected simulated fracturing fluid in the operation S4 in various ways. For example, the processor of the computer control system 21 may determine $V_c$ by the following equations (2) and (3):

$$V_c = S_w V_1 \Phi_0 \quad (2)$$

$$S_w = (V_f - V_3 \Phi_f)/[(V_2 - V_3)\Phi_m] \quad (3)$$

wherein $S_w$ denotes the target water saturation of core of each of the plurality of first core samples and/or each of the plurality of second core samples, and $\Phi_f$ denotes the porosity of the hydraulic sand spreading fractures. The target water saturation of core refers to a proportion of space, e.g., percentage, in the pores of the core sample that is occupied by water. The hydraulic sand spreading fractures refer to fractures produced by the simulated fracturing fluid extruding the core sample.

The method for determining the reasonable soaking time of the shale gas well is illustrated in detail below. The method may include the following operations.

In S1, a downhole core of a shale gas well in a block is selected, i.e., a plurality of first core samples of which surfaces contain natural fractures and a plurality of second core samples of which surfaces do not contain natural fractures are selected; salt washing, oil washing, and drying are performed on the plurality of first core samples and the plurality of second core samples; a length of each of the plurality of first core samples and each of the plurality of second core samples is measured to be 5 cm, a diameter of each of the plurality of first core samples and each of the plurality of second core samples is measured to be 2.5 cm, and a volume of each of the plurality of first core samples and each of the plurality of second core samples is obtained to be $V_1 = 24.5$ cm$^3$. In this embodiment, the porosity Po of both the plurality of first core samples and the plurality of second core samples is measured to be 5%.

In S2, the temperature in the constant temperature room is preset to a temperature 339 K of a reservoir in which the plurality of first core samples and the plurality of second core samples are located. Then, each of the plurality of first core samples is placed in the core gripper 12, the confining pressure pump 18 is activated, and the core confining pressure is applied to the first core sample in the core gripper 12. Applying the core confining pressure using the confining pressure pump 18 is equal to an in-situ effective stress of 16.3 MPa. The core gripper 12 is vacuumized using the vacuum pump 17 to simulate the state of the first core sample in the reservoir.

In S3, the methane is injected into the first core sample in the core gripper 12 using the methane gas cylinder 1 until the pore pressure of the reservoir is reached, and the pressure is maintained for 4 days.

In S4, the simulated fracturing fluid injection pump 14 is activated and 0.614 cm$^3$ of the simulated fracturing fluid is injected into the core gripper 12. The simulated fracturing fluid is MnCl$_2$, and the mass fraction of MnCl$_2$ in the aqueous solution is 5%.

After the simulated fracturing fluid is injected, the third valve 10 is closed.

In S5, the resistivity tester is activated, and the resistivity change curve of the first core sample is measured. At the same time, the half-life period of the pressure attenuation of the first pressure sensor is continuously measured and obtained using the pressure attenuation method until the inflection point appears in the resistivity change curve of the first core sample.

Figure 3:
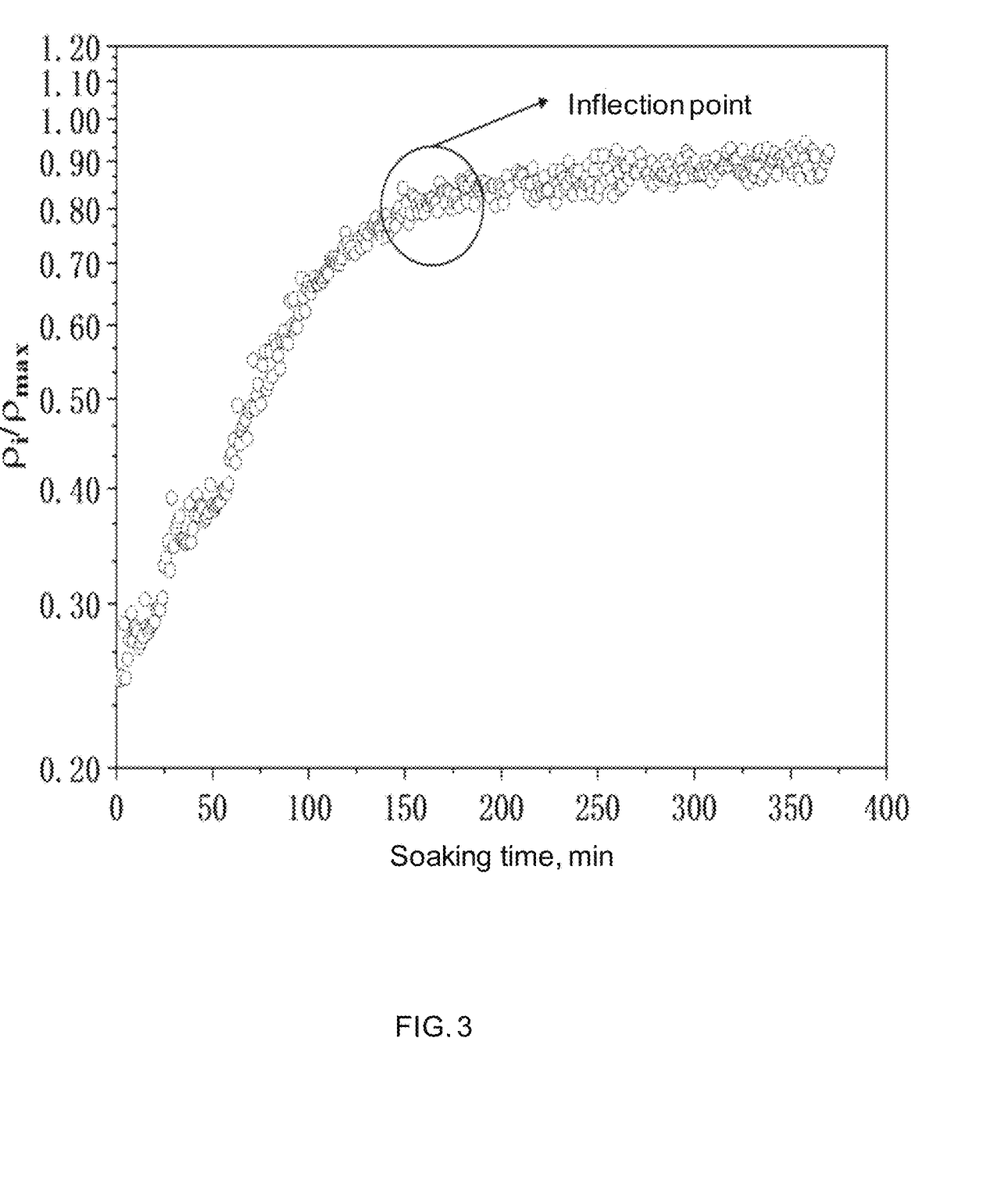
FIG. 3 is a schematic diagram illustrating a relationship between a core resistivity change and a soaking time during an experiment according to some embodiments of the present disclosure.

FIG. 3 is a schematic diagram illustrating a relationship between a core resistivity change and a soaking time during an experiment according to some embodiments of the present disclosure. As shown in FIG. 3, $\rho_i$ denotes the resistivity of a core at a soaking time i; $\rho_{max}$ denotes the maximum resistivity of the core during the soaking time; meanwhile, a half-life period of pressure attenuation of a first pressure sensor is continuously measured and obtained using a pressure attenuation method, i.e., the monitoring of the half-life period of next pressure attenuation begins immediately after the last pressure attenuation reaches the half-life period, until an obvious inflection point appears in the resistivity of the core.

In S6, each of the plurality of first core samples in the core gripper 12 is replaced with each of the plurality of second core samples, and the operations S2-S5 are repeated; and an experimental duration $t_{1f}$=105 min during which each of the plurality of first core samples presents the shortest half-life period of pressure attenuation and an experimental duration $t_{1m}$=135 min during which each of the plurality of second core samples presents the shortest half-life period of pressure attenuation are obtained, respectively.

During a time period between the injection of the simulated fracturing fluid in the operation S4 and the appearance of the inflection point in the resistivity change curve in the operation S5, the methane nuclear magnetic signals of the plurality of first core samples and the plurality of second core samples are continuously monitored using the online NMR tester 9, and a time point $t_{2f}$=78 min at which the core nuclear magnetic signals of the plurality of first core samples have the largest change amplitude and a time point $t_{2m}$=112 min at which the core nuclear magnetic signals of the plurality of second core samples have the largest change amplitude are obtained, respectively.

In S7, the experimental duration $t_{1f}$ during which each of the plurality of first core samples presents the shortest half-life period of pressure attenuation, the experimental duration $t_{1m}$ during which each of the plurality of second core samples presents the shortest half-life period of pressure attenuation, the time point $t_{2f}$ at which the core nuclear magnetic signals of the plurality of first core samples have the largest change amplitude, and the time point $t_{2m}$ at which the core nuclear magnetic signals of the plurality of second core samples have the largest change amplitude are sorted, sorted two intermediate arrays are taken as time endpoints, and a value within the time endpoints is soaking time $t_c$ at a core scale, which is within a range of [105 min, 112 min].

In S8, the soaking time $t_R$ of the shale gas well is obtained based on the soaking time $t_c$ at the core scale, i.e., $t_{1R}$=3.2 days and $t_{2R}$=3.5 days at a gas reservoir scale corresponding to $t_{1f}$=105 min and $t_{2m}$=112 min at the core scale are calculated, respectively, such that the reasonable soaking time $t_R$, which is favorable to the high production of the shale gas well, is within a range of [3.2 days, 3.5 days].

In some embodiments of the present disclosure, by providing the methane gas cylinder, the simulated crude oil injection pump, the resistivity tester, the online NMR tester, the core gripper, the simulated fracturing fluid injection pump, the constant temperature room, the vacuum pump, the confining pressure pump, and the computer control system, and by sufficiently saturating the plurality of first core samples and the plurality of second core samples with methane gas (for the shale gas well) or the simulated crude oil (for the shale oil well) and injecting a certain amount of simulated fracking fluid into the core, the core resistivity changes under different soaking time are measured, and the gas-fluid transmission capacity in the core is tested through the pressure decay experiment. Meanwhile, by monitoring the changes of the location of methane (for the shale gas well) or the crude oil (for the shale oil well) in the core through the online NMR, the impact of the soaking time on the core permeability, and the producing capacity of the matrix methane (for the shale gas well) or the simulated crude oil (for the shale oil well) is evaluated, and finally the soaking time that is conducive to the high and stable production of the shale oil/gas well is determined, providing a basis for the efficient development of the shale oil/gas well. The experimental duration during which each of the plurality of first core samples presents the shortest half-life period of pressure attenuation and the experimental duration during which each of the plurality of second core samples presents the shortest half-life period of pressure attenuation, and the time point at which the core nuclear magnetic signals of the plurality of first core samples have the largest change amplitude and the time point at which the core nuclear magnetic signals of the plurality of second core samples have the largest change amplitude are obtained. The experimental duration during which the shortest half-life period of pressure attenuation is presented refers to a time of maximum core seepage capacity. The time point at which the nuclear magnetic signals have the largest change amplitude refers to a time point when the methane (for the shale gas well) or the simulated crude oil (for the shale oil well) in the matrix core is used to the greatest extent. The purpose and benefits of using the intermediate value in the present disclosure are that both the maximum core seepage capacity and the optimal capacity of using the matrix methane (for the shale gas well) or the simulated crude oil (for the shale oil well) are considered during the time period; the plurality of first core sample of which the surfaces contain the natural fractures and the plurality of second core sample of which the surfaces do not contain the natural fractures are used for testing, separately. During the onsite soaking time period, the process of seepage and suction of the fracturing fluid from the hydraulic fractures into the natural fractures and the base blocks mainly occurs. Accordingly, considering the onsite actual state, i.e.: the natural fractures and the shale base blocks, the first core samples containing the natural fractures and the second core samples not containing the natural fractures are used.

In some embodiments, the method for determining the reasonable soaking time of the shale oil/gas well may further include: in response to determining that a monitoring temperature in the constant temperature room 16 exceeds a hazardous temperature threshold, issuing a first alarm through an audible and visual alarm, the time of issuing the first alarm including a time range in which a sample placement time is located and a time range in which a sample replacement time is located; in response to determining that the sample replacement time is reached, generating a predicted cooling time period; and blocking the constant temperature room 16 and the core gripper 12 during the predicted cooling time period.

The monitoring temperature refers to a real temperature inside the constant temperature room 16. For example, a temperature sensor may collect temperature data of an internal environment of the constant temperature room 16.

In some embodiments, after the temperature in the constant temperature room is preset to a temperature of a reservoir where the plurality of first core samples and the plurality of second core samples are located in the operation S2, the computer control system 21 may control a temperature control device to make temperature adjustment in accordance with the preset temperature such that the temperature in the constant temperature room 16 reaches the temperature of the reservoir where the plurality of first core samples and the plurality of second core samples are located. For example, if the temperature in the constant temperature room 16 is lower than the temperature of the reservoir where the plurality of first core samples and the plurality of second core samples are located, the constant temperature room 16 may be heated by a heating component until the monitoring temperature monitored by the temperature sensor reaches the temperature of the reservoir; conversely, heat dissipation may be performed on the constant temperature room 16 through a heat dissipation fan until the monitoring temperature monitored by the temperature sensor reaches the temperature of the reservoir where the plurality of first core samples and the plurality of second core samples are located.

In some embodiments, in response to determining that a temperature difference between the monitoring temperature in the constant temperature room monitored by the temperature sensor and the preset temperature exceeds a preset difference, the computer control system 21 may control the temperature control device to make temperature adjustment. The preset difference may be set by a technician based on experience. For example, the preset difference may be a maximum fluctuation value of the temperature of the reservoir where the plurality of first core samples and the plurality of second core samples are located.

The hazardous temperature threshold refers to the minimum temperature value that poses a safety risk to the human body, such as the lowest temperature that may cause burns to the human skin. In some embodiments, the hazardous temperature threshold may be obtained by setting based on priori experience.

The first alarm refers to an alarm that is used to warn of possible heat burns, such as a light alarm, a voice alarm, etc.

In some embodiments, the first alarm may be issued through the audible and visual alarm. The audible and visual alarm may include a flash light and a loudspeaker. Merely by way of example, if the monitoring temperature exceeds the hazardous temperature threshold, the computer control system may control the flash light of the audible and visual alarm to emit a specific color of light (e.g., red) and play a voice prompt, such as "Please prevent burns when the temperature is too high" through the loudspeaker, thereby completing the issuance of the first alarm.

The sample placement time refers to a preset time for placing the plurality of first core samples and the plurality of second core samples into the core gripper 12. The sample replacement time refers to a preset time for replacing the plurality of core samples. The time range in which the sample placement time is located and the time range in which the sample replacement time is located refer to time periods before and after the sample placement time and the sample replacement time. The size of the time range may be preset by the technician. It is understood that it is difficult for a tester to perform precisely at the specified sample placement time and sample replacement time when the samples are placed or replaced, and there may be a certain period of advancement or postponement. Therefore, the technician may set the size of the time range based on a fluctuation range of an actual execution time of sample placement and sample replacement in historical data.

In some embodiments, if the monitoring temperature is higher than hazardous temperature threshold, the computer control system 21 may issue the first alarm in the time range in which the sample placement time is loaded and the time range in which the sample replacement time is located, so as to provide a safety alert to the personnel performing the sample placement and the sample replacement to avoid burns.

The predicted cooling time period refers to pre-estimated time period for cooling the constant temperature room 16, such as a time period for turning on the heat dissipation fan of the temperature control device to cool the constant temperature room 16.

In some embodiments, the computer control system 21 may calculate a current temperature change rate based on the latest monitoring temperatures at two adjacent time points; calculate a cooling duration required for a current monitoring temperature to drop to the hazardous temperature threshold based on a difference between the current monitoring temperature and the hazardous temperature threshold, and the current temperature change rate; calculate the predicted cooling time period based on the cooling duration and the current time point, wherein the current monitoring temperature refers to the latest monitoring temperature measured by the temperature sensor. For example, if the latest temperatures at the two adjacent time points are 90° C. corresponding to 10:10 and 86° C. corresponding to 10:12, the current temperature change rate is 2° C. per minute; assuming that the hazardous temperature threshold is 50° C., a duration required for cooling down from the current 86° C. (i.e., the monitoring temperature measured at 10:12) to the hazardous temperature threshold of 50° C. is (86° C.-50° C.)÷2° C./min=18 min, the predicted time period for cooling is 18 min after the current time point, i.e., 10:12-10:30.

In some embodiments, the computer control system 21 may calculate the latest predicted cooling time period based on the latest monitored temperatures at two adjacent time points in real time, and update the predicted cooling time period. For example, the computer control system 21 may display the predicted cooling time period on a screen, and when a new predicted cooling time period is calculated in real time, replace the original predicted cooling time period with the new predicted cooling time period for dynamic updating.

In some embodiments, the computer control system 21 may block the constant temperature room 16 and the core gripper 12 during the predicted cooling time period to prevent the tester from being scalded when the core samples are replaced.

In some embodiments, in response to determining that the temperature change rate is lower than a preset change threshold, the computer control system may turn on the heat dissipation fan of the temperature control device to cool down the constant temperature room to accelerate the cooling rate of the constant temperature room.

The preset change threshold refers to the lowest acceptable temperature change rate. In some embodiments, the preset change threshold may be set by the tester based on test needs. For example, the tester may calculate the lowest acceptable cooling rate as the preset change threshold based on the preset temperature and hazardous temperature thresholds in the constant temperature room at the time of testing, and the maximum cooling duration that does not affect the test result.

In some embodiments, the computer control system 21 may determine the temperature change rate based on the monitoring temperature; determine a temperature warning time point based on the temperature change rate, and generate a temperature warning based on the temperature warning time point to notify the user of the temperature warning time point; in response to determining that the monitoring temperature reaches the temperature preset in the operation S2, generate a pressurization control command and send the pressurization control command to the first valve 3; and automatically open the first valve 3 based on the pressurization control command to inject methane into the plurality of first core samples in the core gripper 12.

The temperature warning time point refers to a time at which the temperature reaches the hazardous temperature threshold.

In some embodiments, the computer control system 21 may calculate the temperature warning time point based on the temperature change rate, the monitoring temperature, and the hazardous temperature threshold. For example, if the current temperature change rate is 4° C./min, the current monitoring temperature is 20° C., and the hazardous temperature threshold is 50° C., a duration required to reach the hazardous temperature threshold is (50° C.-20° C.)÷4°

C./min=7.5 min, and the temperature warning time point is the time after 7.5 min. As another example, the computer control system 21 may establish a temperature change rate table based on historical temperature change rates. The temperature change rate table may include parameters such as ambient temperatures, monitoring temperatures, and power of a heating component in the historical operation data of the test device and the corresponding historical temperature warning time points. The computer control system 21 may retrieve in the temperature change rate table according to the current monitoring temperature, thereby determining the temperature warning time point.

The temperature warning refers to a warning that alerts the user of reaching the hazardous temperature threshold. For example, the temperature warning may include displaying the temperature warning time point to the user through a screen.

In some embodiments, the computer control system 21 may generate a warning command displaying the temperature warning time point, and display the temperature warning time point to the user through the screen based on the warning command to issue the temperature warning.

In some embodiments, the computer control system 21 may calculate the temperature change rate based on the latest monitoring temperature; calculate the temperature warning time point based on the latest calculated temperature change rate; and issue a new temperature warning based on the latest temperature warning time point to display the temperature warning time point to the user in real time.

The pressurization control command refers to a command that controls pressurization of the core gripper 12. In some embodiments, the computer control system 21 may generate, upon the monitoring temperature reaching the preset temperature in the operation S2, an opening command to be sent to the first valve 3 to control the first valve 3 to open to inject methane into the plurality of first core samples in the core gripper 12.

In some embodiments of the present disclosure, by calculating the temperature warning time point and notifying the temperature warning time point to the user, and automatically opening the first valve to inject the methane when the temperature reaches the preset temperature, the convenience and efficiency of the experimental operation can be improved and the safety of the experiment can be guaranteed.

In some embodiments of the present disclosure, the core gripper and the constant temperature room are turned off when the temperature reaches the hazardous temperature threshold, which avoids scalding due to the operation of the tester in a high temperature situation, thereby improving the safety of the experiment.

In some embodiments, in response to determining that a methane gas concentration in the constant temperature room 16 reaches a concentration threshold and/or a gas pressure in the core gripper 12 reaches a pressure threshold, the computer control system 21 may issue a second alarm through the audible and visual alarm; and adjust a methane flow rate through the throttle valve 2, or close the first valve 3.

It is understood that during the process of injecting the methane into the core gripper 12, due to the gradual increase in the gas pressure in the core gripper 12, there may be a small leakage of methane at a pipeline connection, a valve, or other positions, resulting in a small amount of methane gas also being present in the constant temperature room.

The concentration threshold refers to the maximum methane concentration that can be tolerated in the constant temperature room.

In some embodiments, the concentration threshold may be preset by the tester based on experience. For example, the tester may use the lowest methane concentration that may jeopardize the tester or the device as the concentration threshold.

The pressure threshold refers to a maximum gas pressure value that can be accepted in the core gripper. In some embodiments, the pressure threshold may include a pore pressure value of the reservoir where the plurality of first core samples and the plurality of second core samples are located.

In some embodiments, a plurality of concentration thresholds and a plurality of pressure thresholds may be provided. For example, the lowest methane concentration that may jeopardize the tester or the device may be used as the highest concentration threshold, the pore pressure value of the reservoir where the plurality of first core samples and the plurality of second core samples are located may be used as the highest pressure threshold, and a plurality of concentration thresholds that are less than the highest concentration threshold and a plurality of pressure thresholds that are less than the highest pressure threshold may be set.

The second alarm refers to an alarm that is used to warn of excessive methane gas concentration or gas pressure.

In some embodiments, the second alarm may be issued through the audible and visual alarm. Merely by way of example, when the monitoring temperature exceeds the hazardous temperature threshold, the computer control system 21 may control the flash light of the audible and visual alarm to emit a specific color of light (e.g., blue, etc.), and play a voice prompt such as "methane leakage", "gas pressure is too high", etc., through the loudspeaker, thereby completing the issuance of the second alarm.

In some embodiments, when the methane gas concentration in the constant temperature room 16 reaches a different concentration threshold or the gas pressure in the core gripper reaches a different pressure threshold, the computer control system 21 may issue the second alarm of a different degree of severity. The higher the concentration threshold or the pressure threshold that is reached, the higher the intensity of the second alarm. The intensity of the second alarm refers to the strength of the warning from the audible and visual alarm. For example, when the lowest concentration threshold or the lowest pressure threshold is reached, the audible and visual alarm may issue the second alarm through a relatively mild light color and a relatively flat voice prompt; when the highest concentration threshold or the highest pressure threshold is reached, the audible and visual alarm may issue the second alarm through the most conspicuous light color and the most urgent voice prompt (e.g., a continuous loud warning prompt, etc.).

In some embodiments, the computer control system 21 may adjust the methane flow rate based on different concentration thresholds or pressure thresholds reached. For example, the higher the concentration threshold or pressure threshold reached, the greater the magnitude of reducing the methane flow rate. When the highest concentration threshold or the highest pressure threshold is reached, the first valve may be closed.

In some embodiments, in response to determining that pressure change data meets a preset condition, the computer control system 21 may issue a pressure warning through the audible and visual alarm; and adjust the methane flow rate through the throttle valve.

The pressure change data refers to data used to characterize a gas pressure change. For example, the pressure change data may include a pressure change rate in the gas pressure, a difference between the gas pressure and the pore pressure of the reservoir in which the plurality of the core samples are located, etc.

The preset condition refers to a preset determination condition related to the gas pressure. For example, the preset condition may include that the pressure change rate is less than a preset change threshold. The preset change threshold may be set by the tester as desired.

In some embodiments, different test stages may correspond to different preset conditions. For example, during the process of injecting methane gas such that the gas pressure in the core gripper reaches the pore pressure of the reservoir in which the plurality of core samples are located, the preset condition may include that the pressure change rate is less than a theoretical change rate corresponding to an injection rate displayed by the throttle valve. As another example, during the pressure maintenance stage, the preset condition may include that the difference between the gas pressure and the pore pressure of the reservoir in which the plurality of core samples are located continuously increase.

The theoretical change rate refers to theoretical gas pressure change rate with methane gas injected at the indicated injection rate. In some embodiments, the theoretical change rate may be calculated by conversion through a physical relationship based on the injection rate, and a volume of the core gripper. For example, if the injection rate is 5 L/min, an incremental gas pressure in the core gripper caused by each 5 L increase in gas can be calculated based on the volume, thereby obtaining the theoretical change rate corresponding to the injection rate.

The difference between the gas pressure and the pore pressure of the reservoir in which the plurality of core samples are located continuously increasing may include that: a difference between the gas pressure and the pore pressure of the reservoir that is monitored during a preset sampling period of N pressure monitoring devices may continuously increase. The sampling period refers to a time interval between two consecutive collections of the gas pressure by the pressure sensor.

In some embodiments, if the pressure change rate in the gas pressure is less than the preset change threshold, the injection rate of the methane gas may be increased by adjusting through the throttle valve to increase the test efficiency.

In some embodiments, if the corresponding preset condition is met during the injection of the methane gas, the computer control system 21 may control the acoustic and visual alarm to issue the pressure warning to alert the tester to inspect the equipment and the device, and also control the throttle valve to adjust the methane flow rate to 0 or close the first valve to avoid further leakage of the methane gas.

In some embodiments, if the corresponding preset condition is met during the pressure maintenance stage, the computer control system 21 may issue the pressure warning to alert the tester to inspect the equipment and the device.

In some embodiments of the present disclosure, the warning is given and the methane flow rate is adjusted based on the methane gas concentration in the constant temperature room and the gas pressure in the core gripper, such that the test efficiency is improved, and the safety of the testing process is improved.

In some embodiments, the computer control system 21 may also acquire a first sample image and a second sample image based on a photographing device; input the first sample image and the second sample image into an image analysis device to generate fracture distribution information; and screen the first core sample and the second core sample based on the fracture distribution information.

The first sample image refers to an image of each of the plurality of first core samples. The second sample image refers to an image of each of the plurality of second core samples. In some embodiments, the first sample image and the second sample image may include at least two images of side surfaces of each of the plurality of first core samples and each of the plurality of second core samples, respectively. The side surfaces refer to side surfaces of cylindrical first core samples and second core samples, respectively.

The fracture distribution information refers to a distribution of fractures on the plurality of first core samples and the plurality of second core samples. In some embodiments, the fracture distribution information may include information such as a length, a width, a location, and other information of the fractures.

In some embodiments, the image analysis device may determine the fracture distribution information in various ways. For example, the image analysis device may compare each first sample image/second sample image with a standard sample image without fractures, respectively, and determine lines present on the first sample image/second sample image but not present on the standard sample image as fractures, and calculating the length, the width, and the location of the fractures as the fracture distribution information corresponding to the first core sample/the second core sample. The location of the fractures may be represented by the coordinates of a start point, the coordinates of a midpoint, the coordinates of an end point, or the like, of the fractures.

In some embodiments, the image analysis device may determine the fracture distribution information through a core image model. In some embodiments, the core image model may be a machine learning model, such as convolutional neural networks (CNN), etc. In some embodiments, the image analysis device may input one first sample image or one second sample image and the standard sample image into the core image model at a time to be processed to obtain the fracture distribution information.

An input of the core image model may include the core sample image and the standard core image, and an output of the core image model may include the fracture distribution information. The standard core image may be an image of a core sample without fractures.

In some embodiments, the core image model may be obtained by training an initial core image model with a large number of first samples with first labels. The first samples may include a large number of images of real core samples with fractures or real core samples without fractures obtained from the historical data; the first labels may include actual fracture distribution information corresponding to the first samples. The first labels may be manually labeled. For example, the first labels may be manually labeled based on the count and the location of the natural fractures in the first samples.

In some embodiments, the computer control system 21 may process the first sample image and the second sample image into grayscale images, and input the grayscale images into the image analysis device; and the image analysis device may determine the fracture distribution information based on the grayscale images and a standard grayscale image.

The standard grayscale image refers to a grayscale image obtained by corresponding processing of the standard core image. In some embodiments, an image processing device may determine the fracture distribution information based on a comparative analysis of the grayscale images and the standard grayscale image. As another example, the image processing device may also input the grayscale images and the standard grayscale image into the core image model to obtain the fracture distribution information.

In some embodiments of the present disclosure, by processing the first sample image and the second sample image as the grayscale images and determining the fracture distribution information based on the grayscale images, the difficulty in image analysis by the image analysis device can be reduced, and the determination efficiency and accuracy of the fracture distribution information can be improved.

In some embodiments, the computer control system 21 may obtain historical fracture distribution information with an inaccurate test result in the historical data; cluster the historical fracture distribution information based on the location of the fractures in the historical fracture distribution information to obtain a plurality of clustering clusters each of which includes at least one historical fracture distribution information, the mode of clustering including a hierarchical clustering algorithm, a synthetic clustering, and other clustering modes that do not require a preset count of clusters; and screen out the first core sample and the second core sample corresponding to the fracture distribution information of which the distance from the clustering center of the at least one clustering cluster is less than a preset distance threshold.

In some embodiments, a distance between the fracture distribution information and the clustering center may be calculated based on a distance between a fracture location in the fracture distribution information and a fracture location in the clustering center.

In some embodiments, different clustering clusters may correspond to different preset distance thresholds, and the preset distance thresholds corresponding to different clustering clusters may be determined based on a count of historical fracture distribution information in different clustering clusters. The larger the count of historical fracture distribution information in the clustering clusters, the larger the corresponding preset distance threshold. Merely by way of example, the preset $$\text{threshold} = n \times \frac{L}{N};$$

wherein n denotes the count of the historical fracture distribution information in the clustering clusters, L denotes the maximum distance between the historical fracture distribution information in the clustering cluster with the lowest count of historical fracture distribution information and the clustering center, and N denotes the count of historical fracture distribution information in the clustering cluster with the lowest count of historical fracture distribution information.

It can be understood that if the historical fracture distribution information is the fracture distribution information corresponding to the core samples with inaccurate test results in the historical data, the greater the count of historical fracture distribution information in the clustering clusters, the greater the possibility of inaccurate testing of the core samples corresponding to the historical fracture distribution information in the clustering clusters in historical tests, and the more stringent the requirements for the first core sample and the second core sample corresponding to similar fracture distribution information in screening.

In some embodiments of the present disclosure, by analyzing the first sample image and the second sample image through the image processing device to determine the fracture distribution information and filtering the first core sample and the second core sample, the first core sample and the second core sample of which the test results may be inaccurate can be eliminated in advance, thereby improving the accuracy of the test results.

In some embodiments, the computer control system 21 may evaluate a reliability of a soaking time corresponding to different first core samples and second core samples based on monitoring the temperature and the gas pressure in the core gripper 12; in response to determining that the reliability is lower than a reliability threshold, reselect the first core sample and/or the second core sample to perform the method for determining the reasonable soaking time of the shale oil/gas well.

The reliability refers to a numerical value that characterizes the reasonableness of the soaking time.

In some embodiments, the computer control system 21 may statistically count a maximum temperature fluctuation of the monitoring temperature relative to the preset temperature, and a maximum pressure fluctuation of the gas pressure relative to the pore pressure of the reservoir; and determine, based on the maximum temperature fluctuation and the maximum pressure fluctuation, the reliability of the soaking time. The maximum temperature fluctuation refers to the maximum value of a difference between a plurality of monitoring temperatures during the testing process and the preset temperature. The maximum pressure fluctuation refers to the maximum value of a difference between the gas pressure during the pressure maintenance process and the pore pressure of the reservoir. In some embodiments, the greater the maximum temperature fluctuation and the maximum pressure fluctuation, the less the reliability of the soaking time. Merely by way of example, the reliability of the $$\text{soaking time} = 1 - \frac{\Delta T}{T} - \frac{\Delta F}{F},$$

wherein $\Delta T$ denotes the maximum temperature fluctuation, T denotes the preset temperature, $\Delta F$ denotes the maximum pressure fluctuation, and F denotes the pore pressure of the reservoir.

In some embodiments, the reliability threshold may be determined based on historical test records. For example, the computer control system 21 may calculate an average of historical reliabilities of the first core samples and the second core samples corresponding to inaccurate coking times obtained through the historical tests as the reliability threshold.

In some embodiments, the computer control system 21 may determine the reliability of the soaking time through a soaking model based on the monitoring temperature, the gas pressure, and the fracture distribution information.

In some embodiments, the soaking model may include a machine learning model, such as a long short-term memory (LSTM) network, etc.

In some embodiments, an input of the soaking model may include a monitoring temperature sequence, a pressure data sequence, and the fracture distribution information; and an output of the soaking model may include the reliability of the soaking time.

The monitoring temperature sequence refers to a sequence including a plurality of monitoring temperatures in the constant temperature room 16 during the testing process arranged in a temporal order; and the pressure data sequence refers to a sequence including a plurality of gas pressures in the core gripper 12 during the pressure maintenance process arranged in a temporal order.

In some embodiments, the soaking model may be obtained by training an initial soaking model based on a soaking training dataset constructed from a large number of second samples with second labels.

In some embodiments, the second samples may be obtained based on the historical data. For example, historical monitoring temperature sequences, historical pressure data sequences, and historical fracture distribution information of the first core samples and/or the second core samples from the historical data may be used as the second samples. In some embodiments, the second labels may be determined based on the actual reasonableness of the historical soaking time corresponding to the second samples. If the reasonableness of the historical soaking time is reasonable, the second label is 1; if the reasonableness of the historical soaking time is unreasonable, the second label is 0. The reasonableness of the historical soaking time may be determined based on differences between a plurality of historical soaking times obtained by testing a plurality of historical first core samples and a plurality of historical second core samples of the same shale oil-gas well. For example, if an average difference of a plurality of historical soaking times obtained by testing the plurality of historical first core samples and the plurality of historical second core samples of the same shale oil-gas well at a certain historical soaking time exceeds a preset difference magnitude, the historical soaking time is determined to be unreasonable. The preset difference magnitude may be determined by the tester based on priori knowledge. For example, the preset difference magnitude may be determined based on the degree of accuracy with respect to the soaking time. The second labels may be manually labeled.

In some embodiments, the computer control system 21 may select one or more second samples from the soaking training dataset, and input the one or more second samples into the initial soaking model to obtain predicted model outputs corresponding to the one or more second samples; substitute the predicted model outputs corresponding to the one or more second samples and the second labels of the one or more second samples into a predefined formula of a loss function, and calculate a value of the loss function; and inversely update model parameters of the initial soaking model based on the value of the loss function. The updating of the model parameters may be carried out in various ways. For example, the updating may be carried out based on a gradient descent method. When an iteration end condition is satisfied, the iteration may be ended, and a trained soaking model may be obtained.

In some embodiments of the present disclosure, the reliability of the soaking time is determined through the soaking model, and the objective laws between the monitoring temperature sequence, the pressure data sequence, and the reliability of the soaking time can be learnt by the machine learning model over a large number of soaking samples, thereby more accurately evaluating the degree of reasonableness of the soaking time obtained from the test.

In some embodiments of the present disclosure, the reliability of the soaking time is evaluated by the monitoring temperature and the gas pressure, and the first core sample and the second core sample are reselected to be tested when the reliability is low, such that the final soaking time is ensured to be reasonable.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various parts described above may be embodied in a hardware device, it may also be implemented as a software only solution, e.g., an installation on an existing server or mobile device.

For each patent, patent application, patent application publication, or other materials cited in the present disclosure, such as articles, books, specifications, publications, documents, or the like, the entire contents of which are hereby incorporated into the present disclosure as a reference. The application history documents that are inconsistent or conflict with the content of the present disclosure are excluded, and the documents that restrict the broadest scope of the claims of the present disclosure (currently or later attached to the present disclosure) are also excluded. It should be noted that if there is any inconsistency or conflict between the description, definition, and/or use of terms in the auxiliary materials of the present disclosure and the content of the present disclosure, the description, definition, and/or use of terms in the present disclosure is subject to the present disclosure.

Finally, it should be understood that the embodiments described in the present disclosure are only used to illustrate the principles of the embodiments of the present disclosure. Other variations may also fall within the scope of the present disclosure. Therefore, as an example and not a limitation, alternative configurations of the embodiments of the present disclosure may be regarded as consistent with the teaching of the present disclosure. Accordingly, the embodiments of the present disclosure are not limited to the embodiments introduced and described in the present disclosure explicitly.

What is claimed is:

1. A method for determining a soaking time of a shale gas well, implementing testing and experimentation using a device for testing the soaking time of the shale gas well, wherein the device for testing the soaking time of the shale gas well comprises an online nuclear magnetic resonance (NMR) tester, a core gripper disposed on the online NMR tester, a resistivity tester connected to the core gripper, a methane gas cylinder connected with an inlet of the core gripper, a simulated fracturing fluid injection pump connected with the inlet of the core gripper, a nitrogen gas cylinder connected with the inlet of the core gripper, a first pressure sensor connected with the inlet of the core gripper, a vacuum pump connected with the core gripper, a confining pressure pump connected with the core gripper, a second pressure sensor connected with the core gripper, a throttle valve connected with an outlet of the methane gas cylinder, a first valve connected with an outlet of the throttle valve, a third valve connected with an outlet of the first valve, a fifth valve connected with an outlet of the core gripper, and a computer control system electrically connected with the first pressure sensor, the second pressure sensor, and the core gripper, respectively, wherein a core sample to be tested is placed in the core gripper, a resistivity tester is configured to detect the resistivity of the core sample to be tested in the core gripper, and the online NMR tester and the core gripper are disposed in a constant temperature room;

the method for determining the soaking time of the shale gas well comprises:

S1, selecting a plurality of first core samples of which surfaces contain natural fractures and a plurality of second core samples of which surfaces do not contain the natural fractures, respectively; performing salt washing, oil washing, and drying on the plurality of first core samples and the plurality of second core samples; measuring lengths and diameters of the plurality of first core samples and the plurality of second core samples, and obtaining volumes of the plurality of first core samples and the plurality of second core samples, respectively; and measuring and obtaining porosity $\Phi_0$ of the plurality of first core samples and the plurality of second core samples, respectively;

S2, presetting a temperature in the constant temperature room to a temperature of a reservoir in which the plurality of first core samples and the plurality of second core samples are located, placing each of the plurality of first core samples in the core gripper, activating the confining pressure pump, and applying a core confining pressure to each of the plurality of first core samples in the core gripper; vacuumizing the core gripper using the vacuum pump to simulate a state of each of the first core samples in the reservoir;

S3, injecting methane into each of the plurality of first core samples in the core gripper using the methane gas cylinder until a pore pressure of the reservoir is reached, and maintaining the pore pressure for 4 days;

S4, activating the simulated fracturing fluid injection pump and injecting simulated fracturing fluid into the core gripper; and closing the third valve;

S5, activating the resistivity tester to measure a resistivity change curve of each of the plurality of first core samples; and continuously measuring and obtaining a half-life period of pressure attenuation of the first pressure sensor using a pressure attenuation method at a same time until an inflection point appears in the resistivity change curve of each of the plurality of first core samples;

S6, replacing each of the plurality of first core samples in the core gripper with each of the plurality of second core samples, and repeating operations S2-S5; and obtaining an experimental duration $t_{1f}$ during which each of the plurality of first core samples presents a shortest half-life period of pressure attenuation and an experimental duration $t_{1m}$ during which each of the plurality of second core samples presents the shortest half-life period of pressure attenuation, respectively;

during a time period between the injection of the simulated fracturing fluid in operation S4 and the appearance of the inflection point in the resistivity change curve in operation S5, continuously monitoring methane nuclear magnetic signals of the plurality of first core samples and the plurality of second core samples using the online NMR tester, and obtaining a time point $t_{2f}$ at which core nuclear magnetic signals of the plurality of first core samples have a largest change amplitude and a time point $t_{2m}$ at which the core nuclear magnetic signals of the plurality of second core samples have the largest change amplitude, respectively;

S7, sorting the experimental duration $t_{1f}$ during which each of the plurality of first core samples presents the shortest half-life period of pressure attenuation, the experimental duration $t_{1m}$ during which each of the plurality of second core samples presents the shortest half-life period of pressure attenuation, the time point $t_{2f}$ at which the core nuclear magnetic signals of the plurality of first core samples have the largest change amplitude, and the time point $t_{2m}$ at which the core nuclear magnetic signals of the plurality of second core samples have the largest change amplitude, taking sorted two intermediate arrays as time endpoints, and a value within the time endpoints being soaking time $t_c$ at a core scale; and S8, obtaining soaking time $t_R$ of the shale gas well based on the soaking time $t_c$ at the core scale, which is expressed as:

$$t_R = t_c \frac{(V_2 - V_3)\Phi_m}{V_1 \Phi_0} \times \frac{V_c}{V_f}$$

wherein $V_2$ denotes a total volume of reservoir reconstruction by hydraulic fracturing; $V_3$ denotes a total volume of sand spreading fractures formed in the reservoir after the hydraulic fracturing; $V_c$ denotes a volume of the simulated fracturing fluid injected to establish a target water saturation of the core sample; $V_1$ denotes a volume of each of the plurality of first core samples or each of the plurality of second core samples; $V_f$ denotes a volume of fracturing fluid pumped for onsite hydraulic fracturing construction; and $\Phi_m$ denotes a reservoir porosity after hydraulic fractures are removed from a total reconstruction region of the hydraulic fracturing.

2. The method of claim 1, wherein a second valve, a buffer container, and a fourth valve are connected in series between the nitrogen gas cylinder and the core gripper.

3. The method of claim 1, wherein a sixth valve is provided between the simulated fracturing fluid injection pump and the third valve.

4. The method of claim 1, wherein a seventh valve is provided on the confining pressure pump.

5. The method of claim 1, wherein the volume of the simulated fracturing fluid injected in the operation S4 is expressed as:

$$V_c = S_w V_1 \Phi_0$$

$$S_w = (V_f - V_3 \Phi_f)/[(V_2 - V_3)\Phi_m]$$

wherein $S_w$ denotes the target water saturation of the core sample of at least one of each of the plurality of first core samples and each of the plurality of second core samples; and $\Phi_f$ denotes a porosity of the hydraulic sand spreading fractures.

* * * * *